US010308580B2

(12) United States Patent
Rüdenauer et al.

(10) Patent No.: US 10,308,580 B2
(45) Date of Patent: *Jun. 4, 2019

(54) PROCESS FOR PREPARING AN ARYLPROPENE

(71) Applicant: BASF SE, Ludwigshafen am Rhein (DE)

(72) Inventors: Stefan Rüdenauer, Weinheim (DE); Andreas Lanver, Mannheim (DE); Ralf Pelzer, Fürstenberg (DE); Klaus Ebel, Heddesheim (DE); Thomas Fenlon, Mannheim (DE); Andrei-Nicolae Parvulescu, Ruppertsberg (DE); Sumana Chaturvedula, Frankfurt (DE)

(73) Assignee: BASF SE (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/744,474

(22) PCT Filed: Jul. 15, 2016

(86) PCT No.: PCT/EP2016/066939
§ 371 (c)(1),
(2) Date: Jan. 12, 2018

(87) PCT Pub. No.: WO2017/009462
PCT Pub. Date: Jan. 19, 2017

(65) Prior Publication Data
US 2018/0208533 A1 Jul. 26, 2018

(30) Foreign Application Priority Data
Jul. 15, 2015 (EP) ..................... 15176821

(51) Int. Cl.
C07C 41/18 (2006.01)

(52) U.S. Cl.
CPC .................. C07C 41/18 (2013.01)

(58) Field of Classification Search
CPC .................................... C07C 41/18
See application file for complete search history.

(56) References Cited

U.S. PATENT DOCUMENTS

| 2,373,982 | A | 4/1945 | Sturrock et al. |
| 4,026,951 | A | 5/1977 | Bauer et al. |
| 4,456,582 | A | 6/1984 | Marosi et al. |
| 9,446,390 | B2 | 9/2016 | Parvulescu et al. |
| 9,540,305 | B2 | 1/2017 | Parvulescu et al. |
| 9,688,648 | B2 | 6/2017 | Teles et al. |
| 9,695,099 | B2 | 7/2017 | Liu et al. |
| 9,725,428 | B2 | 8/2017 | Teles et al. |
| 9,738,616 | B2 | 8/2017 | Riedel et al. |
| 9,765,001 | B2 | 9/2017 | Rüdenauer et al. |
| 9,765,003 | B2 | 9/2017 | Vautravers et al. |
| 9,856,199 | B2 | 1/2018 | Hickmann et al. |
| 9,920,007 | B2 | 3/2018 | Rudenauer et al. |
| 2016/0186008 | A1 | 6/2016 | Klopsch et al. |
| 2016/0250624 | A1 | 9/2016 | Parvulescu et al. |
| 2016/0256859 | A1 | 9/2016 | Parvulescu et al. |
| 2016/0264543 | A1 | 9/2016 | Vautravers et al. |
| 2016/0279621 | A1 | 9/2016 | Parvulescu et al. |
| 2016/0332152 | A1 | 11/2016 | Parvulescu et al. |
| 2017/0037020 | A1 | 2/2017 | Rudenauer et al. |
| 2017/0037021 | A1 | 2/2017 | Stork et al. |
| 2017/0037022 | A1 | 2/2017 | Stork et al. |
| 2017/0037296 | A1 | 2/2017 | Kimura et al. |
| 2017/0044421 | A1 | 2/2017 | Parvulescu et al. |
| 2017/0233780 | A1 | 8/2017 | Breuer et al. |
| 2017/0233874 | A1 | 8/2017 | Aust et al. |
| 2017/0246620 | A1 | 8/2017 | Parvulescu et al. |
| 2017/0275225 | A1 | 9/2017 | Riedel et al. |
| 2017/0283352 | A1 | 10/2017 | Fenlon et al. |
| 2017/0292084 | A1 | 10/2017 | Stork et al. |
| 2017/0298034 | A1 | 10/2017 | Riedel et al. |
| 2017/0334820 | A1 | 11/2017 | Pelzer et al. |
| 2017/0334824 | A1 | 11/2017 | Pelzer et al. |
| 2017/0362532 | A1 | 12/2017 | Pelzer et al. |
| 2018/0002266 | A1 | 1/2018 | Bru Roig et al. |
| 2018/0036723 | A1 | 2/2018 | Riedel et al. |
| 2018/0044313 | A1 | 2/2018 | Rudenauer et al. |

FOREIGN PATENT DOCUMENTS

| CN | 102491884 A | 6/2012 |
| CN | 103058835 A | 4/2013 |
| DE | 2418974 B1 | 9/1975 |
| EP | 0007081 A1 | 1/1980 |
| GB | 1444897 A | 8/1976 |
| SU | 261380 | 1/1970 |
| SU | 355144 | 1/1972 |
| WO | WO-2013117536 A2 | 8/2013 |
| WO | WO-2013117537 A1 | 8/2013 |
| WO | WO-2014122152 A1 | 8/2014 |

(Continued)

OTHER PUBLICATIONS

International Search Report for PCT/EP2016/066923 dated Sep. 27, 2016.
International Search Report for PCT/EP2016/066939 dated Sep. 13, 2016.
Written Opinion of the International Searching Authority for PCT/EP2016/066923 dated Sep. 27, 2016.
Written Opinion of the International Searching Authority for PCT/EP2016/066939 dated Sep. 13, 2016.
International Preliminary Report on Patentability with Written Opinion for International Application No. PCT/EP2016/066939, dated Jan. 16, 2018.

(Continued)

Primary Examiner — Rosalynd A Keys
(74) Attorney, Agent, or Firm — Drinker Biddle & Reath LLP

(57) ABSTRACT

A process for preparing an arylpropene from a diarylpropane by gas phase thermolysis in the presence of solid porous catalyst comprising silica having large pore volume and low acidity.

21 Claims, No Drawings

(56) References Cited

FOREIGN PATENT DOCUMENTS

| WO | WO-2015018793 A1 | 2/2015 |
|----|------------------|--------|
| WO | WO-2015025250 A1 | 2/2015 |
| WO | WO-2015025268 A1 | 2/2015 |
| WO | WO-2015083113 A1 | 6/2015 |
| WO | WO-2015107156 A2 | 7/2015 |
| WO | WO-2016050836 A1 | 4/2016 |

OTHER PUBLICATIONS

U.S. Appl. No. 15/316,220.
U.S. Appl. No. 15/521,924.
U.S. Appl. No. 15/537,128, filed Jun. 6, 2017.
U.S. Appl. No. 15/557,370, filed Sep. 11, 2017.
U.S. Appl. No. 15/571,107, filed Nov. 1, 2017.
U.S. Appl. No. 15/575,169, filed Nov. 17, 2017, Rüdenauer et al.
U.S. Appl. No. 15/577,590, filed Nov. 28, 2017, Schein-Albrecht et al.
U.S. Appl. No. 15/577,570, filed Nov. 28, 2017.
U.S. Appl. No. 15/578,959, filed Dec. 1, 2017.
U.S. Appl. No. 15/743,153, filed Jan. 9, 2018.
U.S. Appl. No. 15/744,324, filed Jan. 12, 2018.
International Search Report for International Application No. PCT/DK2016/050188, dated Sep. 16, 2016.
Innes, R., et al., "p-Methylstryrene from toluene and acetaldehyde", Journal of Molecular Catalysis, 1985, vol. 32, No. 2, pp. 259-271.
Niwa, M., et al., "Measurements of acidic property of zeolites by temperature programmed desorption of ammonia", Catalysis Surveys From Japan, 1997, vol. 1, No. 2, pp. 215-226.
Bauer, K., et al., "Common Fragrance and Flavor Material", 4th Edition, Wiley-VCH, 2001, pp. 1-300.
Maslozhirovaya Promyshlennost, 1974, vol. 9, pp. 29-30.

PROCESS FOR PREPARING AN ARYLPROPENE

CROSS-REFERENCE TO RELATED APPLICATIONS

This application is a national stage application (under 35 U.S.C. § 371) of PCT/EP2016/066939, filed Jul. 15, 2016, which claims benefit of European Application No. 15176821.5, filed Jul. 15, 2015, both of which are incorporated herein by reference in their entirety.

The present invention relates to a gas phase thermolysis process for preparing an arylpropene from a diarylpropane in the presence of solid porous catalyst comprising silica having large pore volume and low acidity.

Anethole, due to its characteristic anise smell, is of significant commercial interest as a fragrance and as a flavouring substance. In particular, anethole is used as a fragrance in detergents and cleaning agents as well as a flavouring substance in the food industry.

Certain synthesis procedures for preparing anethole are known in the art. For example, anethole can be prepared from natural sources such as fennel oil or anise oil. Reference is made, for example, to CN 102491884 A. However, the preparation of fragrances from natural sources is often expensive, and the amounts obtainable by this processes are only limited. Further, the purity or the obtained amounts of these fragrances often vary due to changing environmental conditions. Therefore, there is a need to at least partially replace said natural sources by synthetically obtainable compounds.

With regard to such synthetically obtainable compounds, Bauer et al., Common Fragrance and Flavor Materials, 2001, 4th Edition, Wiley-VHC, describes the preparation of anethole by a process which comprises the base catalyzed re-arrangement of 1-allyl-4-methoxybenzene (estragole). Methods comprising a Friedel-Crafts acylation of methoxybenzene (anisole) with propionic acid halides or propionic acid anhydride followed by the reduction of the carbonyl group and the subsequent elimination of water are disclosed in SU 261380 and SU 355144. The acylation of anisole with propionic acid anhydride with $ZnCl_2$ and $FeCl_3$ is described in Maslozhirovaya Promyshlennost (1974), volume 9, pages 29-30. CN 103058835 A describes a process for the synthesis of anethole via a Friedel-Crafts reaction starting from anisole and propionic acid chloride, followed by the reduction of th carbonyl group to obtain the corresponding alcohol using $NaBH_4$ and the subsequent elimination of water. DE 2418974 B1 describes a process for the preparation of anethole wherein, in a first step, anisole is condensed with propionic aldehyde in the presence of acidic catalysts to obtain a mixture of bis-(methoxyphenyl) propanes, and in a second step, the condensation products are decomposed in the liquid phase in the presence of catalytic amounts of acid at a a temperature of from 100 to 300° C. to obtain trans-anethole, cis-anethole and anisole; it is a disadvantage of this process that the bis-(methoxyphenyl) propanes are not completely decomposed; additionally, only moderate yields regarding anethole are obtained; yet further, the long exposure time of the bis-(methoxyphenyl) propanes at elevated temperatures leads to an increased amount of by-products, non-desired isomers as well as oligomers and polymers.

Therefore, it was an object of the present invention to provide an improved process for preparing arylpropenes, in particular anethole, wherein the above discussed disadvantages are avoided. It was a further object of the present invention that this process is simple and efficient in order to provide the possibility to produce arylpropenes, in particular anethole, in a cost-effective manner. It was a further object of the present invention that this process exhibits a high selectivity with regard to a specific isomer of the arylpropenes, in particular to trans-anethole.

Surprisingly, it was found that these objects can be solved if in a gas phase thermolysis reaction wherein a 1,1-diarylpropane is decomposed to the respective arylpropene, a solid porous catalyst is employed which comprises, as catalytically active material, silica which exhibits a specific acidity and, simultaneously, a specific pore volume, in particular silica which exhibits a specifically low acidity and, simultaneously, a specifically high pore volume.

Therefore, the present invention relates to a process for preparing a compound of formula (I)

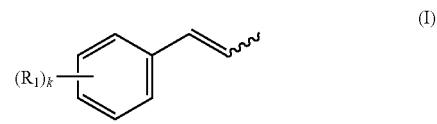

comprising contacting a compound of formula (II)

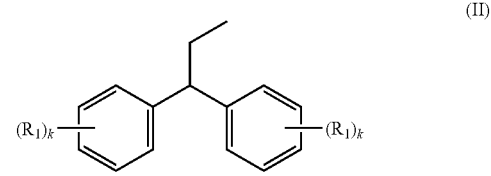

in the gas phase with a solid porous catalyst comprising silica, wherein k is, independently from each other, 0, 1, 2 or 3;
$R_1$ is, independently from each other, hydroxy, $C_1$-$C_6$ alkoxy, di($C_1$-$C_6$-alkyl) aminyl;
wherein the catalyst has a pore volume of at least 0.5 $cm^3$/g as determined by Hg porosimetry according to DIN 66133, and an acidity characterized by an amount of adsorbed ammonia of at most 0.1 mmol/g(catalyst) as determined by $NH_3$-TPD, in particular as determined by $NH_3$-TPD at an ammonia adsorption at 100° C. and an ammonia desorption at 600° C., in particular an ammonia desorption achieved by heating from 100° C. to 600° C. at a heating rate of 10 K/min and holding for 30 min under a He flow of 30 $cm^3$/min, as described in Reference Example 2.1 herein.

Further, it was found that by carrying out the process in the gas phase in the presence of the solid porous catalyst comprising silica, high temperatures are possible which allow to minimize the exposure time in the reaction zone in which the reaction is carried out. Therefore, it was possible to minimize the formation of by-products and side-products. In particular, it was found that the combination of the gas phase reaction with the solid porous catalyst comprising silica leads to highly selective process with regard to the formation of the trans-isomer of the compound of formula (I-a), preferably trans-anethole. These advantages could be realized based on a high conversion of the starting material, the compound of formula (II), although, as mentioned above, the exposure time in the reaction zone was short.

It is preferred that the acidity of the catalyst is further characterized in that, as determined by $NH_3$-TPD as described above, at least 95%, preferably at least 98%, more preferably at least 99%, more preferably 99.5%, more preferably at least 99.9% of the ammonia is desorbed at temperatures of at most 250° C., preferably of at most 225° C., more preferably of at most 200° C. This means that the preferred catalyst has essentially no strong acid sites and only some residual acidity.

It is preferred that the pore volume of the catalyst is in the range of from 0.5 to 2.0 cm$^3$/g, more preferably in the range of from 0.6 to 1.2 cm$^3$/g, more preferably in the range of from 0.7 to 1.1 cm$^3$/g, more preferably in the range of from 0.8 to 1.0 cm$^3$/g. The acidity characterized by an amount of adsorbed ammonia is preferably in the range of from 0.01 to 0.09 mmol/g(catalyst), more preferably in the range of from 0.01 to 0.08 mmol/g(catalyst), more preferably in the range of from 0.01 to 0.07 mmol/g(catalyst), more preferably in the range of from 0.01 to 0.06 mmol/g(catalyst), more preferably in the range of from 0.02 to 0.05 mmol/g(catalyst).

A preferred catalyst of the present invention has a pore volume in the range of from 0.5 to 2.0 cm$^3$/g and an acidity characterized by an amount of adsorbed ammonia in the range of from 0.01 to 0.09 mmol/g(catalyst). A more preferred catalyst has a pore volume in the range of from 0.5 to 1.5 cm$^3$/g and an acidity characterized by an amount of adsorbed ammonia in the range of from 0.01 to 0.08 mmol/g(catalyst). A more preferred catalyst has a pore volume in the range of from 0.6 to 1.2 cm$^3$/g and an acidity characterized by an amount of adsorbed ammonia in the range of from 0.01 to 0.07 mmol/g(catalyst). A more preferred catalyst has a pore volume in the range of from 0.7 to 1.1 cm$^3$/g and an acidity characterized by an amount of adsorbed ammonia in the range of from 0.01 to 0.06 mmol/g(catalyst). A more preferred catalyst has a pore volume in the range of from 0.8 to 1.0 cm$^3$/g and an acidity characterized by an amount of adsorbed ammonia in the range of from 0.02 to 0.05 mmol/g(catalyst).

With regard to the chemical composition of the catalyst, no specific restrictions exist provided that the catalyst has the above-described pore volumes and the above-described acidity characterized by an amount of adsorbed ammonia. Preferably, at least 75 weight-%, more preferably at least 90 weight-%, more preferably at least 95 weight-% more preferably at least 99 weight-%, more preferably at least 99.5 weight-% of the catalyst consist of silica.

Therefore, a preferred catalyst of the present invention has a pore volume in the range of from 0.5 to 2.0 cm$^3$/g and an acidity characterized by an amount of adsorbed ammonia in the range of from 0.01 to 0.09 mmol/g(catalyst), wherein preferably, at least 75 weight-%, more preferably at least 90 weight-%, more preferably at least 95 weight-% more preferably at least 99 weight-%, more preferably at least 99.5 weight-% of the catalyst consist of silica. A more preferred catalyst has a pore volume in the range of from 0.5 to 1.5 cm$^3$/g and an acidity characterized by an amount of adsorbed ammonia in the range of from 0.01 to 0.08 mmol/g(catalyst), wherein preferably, at least 75 weight-%, more preferably at least 90 weight-%, more preferably at least 95 weight-% more preferably at least 99 weight-%, more preferably at least 99.5 weight-% of the catalyst consist of silica. A more preferred catalyst has a pore volume in the range of from 0.6 to 1.2 cm$^3$/g and an acidity characterized by an amount of adsorbed ammonia in the range of from 0.01 to 0.07 mmol/g(catalyst), wherein preferably, at least 75 weight-%, more preferably at least 90 weight-%, more preferably at least 95 weight-% more preferably at least 99 weight-%, more preferably at least 99.5 weight-% of the catalyst consist of silica. A more preferred catalyst has a pore volume in the range of from 0.7 to 1.1 cm$^3$/g and an acidity characterized by an amount of adsorbed ammonia in the range of from 0.01 to 0.06 mmol/g(catalyst), wherein preferably, at least 75 weight-%, more preferably at least 90 weight-%, more preferably at least 95 weight-% more preferably at least 99 weight-%, more preferably at least 99.5 weight-% of the catalyst consist of silica. A more preferred catalyst has a pore volume in the range of from 0.8 to 1.0 cm$^3$/g and an acidity characterized by an amount of adsorbed ammonia in the range of from 0.02 to 0.05 mmol/g(catalyst), wherein preferably, at least 75 weight-%, more preferably at least 90 weight-%, more preferably at least 95 weight-% more preferably at least 99 weight-%, more preferably at least 99.5 weight-% of the catalyst consist of silica.

It is possible that the catalyst of the present invention comprises other elements, or compounds such as oxides. Preferred oxides include, but are not restricted to, alkali metal oxides and alkaline earth metal oxides. Among the alkali metal oxides, sodium oxide is preferred. Therefore, the present invention also relates to the process as described above wherein the catalyst comprises one or more alkali metal oxides, preferably sodium oxide, preferably in an amount of at most 0.5 weight-%, more preferably in an amount in the range of from 0.01 to 0.5 weight-%, more preferably in an amount in the range of from 0.05 to 0.4 weight-%, more preferably in an amount in the range of from 0.1 to 0.3 weight-%, based on the weight of the catalyst.

As described hereinunder in detail, the process of the present invention is preferably carried out in continuous mode. For said continuous process, it is preferred that the solid porous catalyst comprising silica is employed in the form of moldings. As to the geometry of the moldings, no specific restrictions exist. Geometries such as strands, for example having rectangular, triangular hexagonal, quadratic, oval, or circular cross-section, stars, tablets, spheres, hollow cylinders, and the like are possible. A preferred geometry of the moldings is a strand having circular cross-section. Such a geometry is preferred if the moldings are employed, for example, as fixed-bed catalyst or fluidized-bed catalyst, more preferably in continuous-type reactions. The diameter of these strands having circular cross-section which can be prepared, e.g., via extrusion processes, is preferably in a range of from 1 to 5 mm, more preferably from 1.5 to 5 mm, more preferably from 1.5 to 4 mm, such as, for example, in the range of from 1.5 to 2.5 mm or in the range of from 2 to 3 mm or in the range of from 2.5 to 3.5 mm or in the range of from 3 to 4 mm.

The compound of formula (II) can be prepared according any conceivable and suitable process. Suitably processes are described, for example, in DE 2418974 B1.

The term "$C_1$-$C_6$ alkoxy" as used in the context of the present invention relates to a linear or branched alkyl residue having 1, 2, 3, 4, 5, or 6 carbon atoms wherein the alkyl residue is linked to the phenyl residue via an oxygen atom. Preferred $C_1$-$C_6$ alkoxy residues include methoxy, ethoxy, n-propoxy, 1-methylethoxy, n-butoxy, 1-methylpropoxy, 2-methylpropoxy, 1,1-dimethylethoxy, n-pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, 1-ethyl-2- methylpropoxy. If a residue $R_1$ is $C_1$-$C_6$ alkoxy, it is preferably $C_1$-$C_5$, more preferably $C_1$-$C_4$ alkoxy, more preferably $C_1$-$C_3$ alkoxy, more preferably $C_1$-$C_2$ alkoxy. If $R_1$ is $C_1$-$C_6$ alkoxy, it is more preferably methoxy.

The term "di($C_1$-$C_6$-alkyl) aminyl" as used in the context of the present invention relates to a residue wherein 1 first $C_1$-$C_6$-alkyl group and a second $C_1$-$C_6$-alkyl group are linked via a nitrogen atom to the phenyl residue. The term "$C_1$-$C_6$-alkyl" as used in the context of the present invention relates to a linear or branched alkyl residue having 1, 2, 3, 4, 5, or 6 carbon atoms. Further, the first $C_1$-$C_6$-alkyl group can be identical to or different from the second $C_1$-$C_6$-alkyl group. In preferred di($C_1$-$C_6$-alkyl) aminyl residues, the $C_1$-$C_6$-alkyl includes methyl, ethyl, propyl, isopropyl, n-butyl, isobutyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl. If a residue $R_1$ is di($C_1$-$C_6$-alkyl) aminyl, the $C_1$-$C_6$-alkyl is preferably $C_1$-$C_5$ alkyl, more preferably $C_1$-$C_4$ alkyl, more preferably $C_1$-$C_3$ alkyl.

With regard to the position of the phenyl residue at which a given residue R1 is located, no specific restrictions exist. Generally, it is conceivable that a given residue $R_1$ is located at every suitably ortho- and/or meta- and/or para-position. Further, it is conceivable that one of the phenyl residues of the compound of formula (II) has 0 or 1 or 2 or 3 residues $R_1$ which may be the same or different from each other, and the other phenyl residue of the compound of formula (II) has 0 or 1 or 2 or 3 residues $R_1$ which may be the same or different from each other.

More preferably, a given residue $R_1$ is hydroxy or methoxy. More preferably, each $R_1$ is methoxy.

Preferably, at least one of the phenyl residues of the compound of formula (II) has one (single) residue $R_1$ which, more preferably, is located at the para-position. More preferably, each of the two phenyl residues of the compound of formula (II) has one (single) residue $R_1$ which, more preferably, is located at the para-position wherein the residues $R_1$ may be the same or different from each other, wherein it is more preferred that the two residues $R_1$ are the same.

Therefore, the present invention preferably relates to the process as described above wherein the compound of formula (I) is a compound of formula

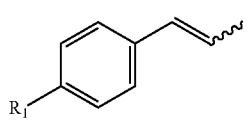

(I)

and the compound of formula (II) is a compound of formula

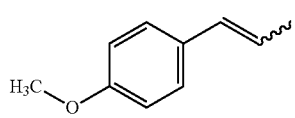

(II)

wherein the two residues $R_1$ according to formula (II) are preferably the same.

Further preferably, the present invention relates to the process as described above wherein the compound of formula (I) is a compound of formula

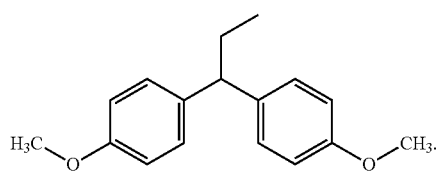

(I)

and the compound of formula (II) is a compound of formula

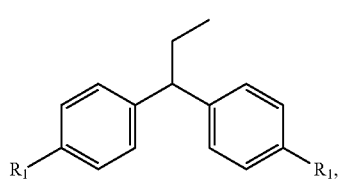

(II)

In particular in case the compound of formula (II) is a compound of formula

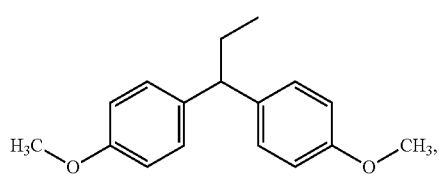

(II)

preferably

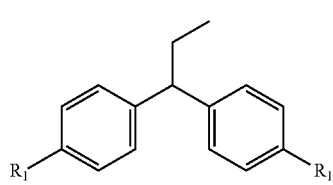

(II)

the starting material which is subjected to the contacting with the solid porous catalyst comprising silica is optionally a mixture comprising the compound of formula (II), i.e. the para/para-substituted (pp) dimer, the ortho/para-substituted (op) dimer of formula (II-b)

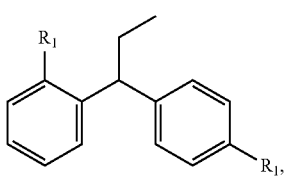

(II-b)

preferably

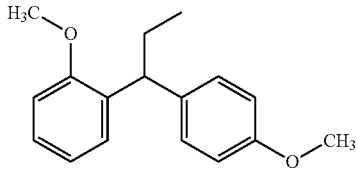
(II-b)

and the ortho/ortho-substituted (oo) dimer of formula (II-c)

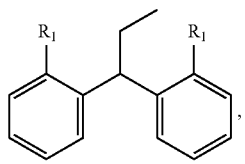
(II-c)

preferably

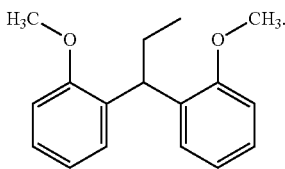
(II-c)

Preferably, the molar ratio of (II) relative to the sum of (II), (II-b) and (II-c) is in the range of from 65 to 75%, the molar ratio of (II-b) relative to the sum of (II), (II-b) and (II-c) is in the range of from 25 to 30%, and the molar ratio of (II-c) relative to the sum of (II), (II-b) and (II-c) is in the range of from 1 to 5%, wherein for a given mixture, these molar ratios add up to 100%. A specifically preferred mixture comprises from 69 to 71% (II) such as 70% (II), from 27 to 29% (II-b), such as 28% (II-b), and from 1 to 3% (II-c), such as 2% (II-c), in each based on the sum of (II), (II-b) and (II-c).

Therefore, the present invention also relates to a process as described above wherein the compound of formula (I) is a compound of formula

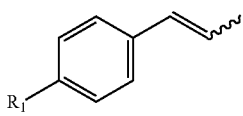
(I)

and the compound of formula (II) is a compound of formula

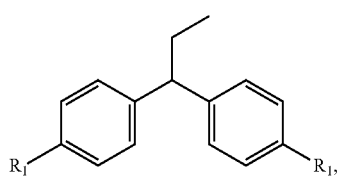
(II)

wherein the two residues $R_1$ according to formula (II) are preferably the same, and wherein, prior to the contacting with the solid porous catalyst comprising silica, the gas phase comprises, in addition to the compound of formula (II), the compound of formula (II-b)

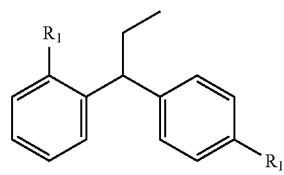
(II-b)

and the compound of formula (II-c)

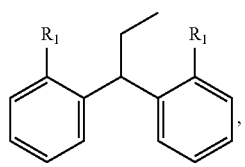
(II-c)

wherein the molar ratio of (II) relative to the sum of (II), (II-b) and (II-c) is preferably in the range of from 65 to 75%, the molar ratio of (II-b) relative to the sum of (II), (II-b) and (II-c) is preferably in the range of from 25 to 30%, and the molar ratio of (II-c) relative to the sum of (II), (II-b) and (II-c) is preferably in the range of from 1 to 5% wherein more preferably, these molar ratios add up to 100%.

Further preferably, the present invention relates to the process as described above wherein the compound of formula (I) is a compound of formula

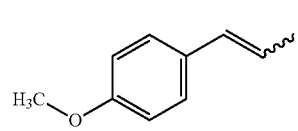
(I)

and the compound of formula (II) is a compound of formula

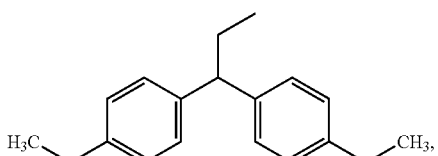
(II)

wherein, prior to the contacting with the solid porous catalyst comprising silica, the gas phase comprises, in addition to the compound of formula (II), the compound of formula (II-b)

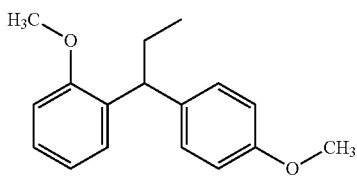

and the compound of formula (II-c)

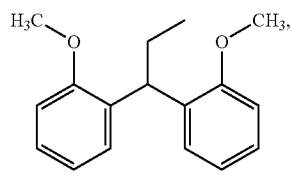

wherein the molar ratio of (II) relative to the sum of (II), (II-b) and (II-c) is preferably in the range of from 65 to 75%, the molar ratio of (II-b) relative to the sum of (II), (II-b) and (II-c) is preferably in the range of from 25 to 30%, and the molar ratio of (II-c) relative to the sum of (II), (II-b) and (II-c) is preferably in the range of from 1 to 5% wherein more preferably, these molar ratios add up to 100%.

Preferably, the contacting of the compound of formula (II) with the solid porous catalyst comprising silica is carried out under thermolytic conditions. The temperature of the gas phase at which said contacting is carried out is preferably at least 250° C., more preferably in the range of from 250 to 650° C., more preferably in the range of from 260 to 600° C., more preferably in the range of from 270 to 550° C., more preferably in the range of from 280 to 500° C., more preferably in the range of from 290 to 450° C., more preferably in the range of from 300 to 400° C. Preferred ranges are, for example, of from 300 to 350° C. or from 325 to 375° C. or from 350 to 400° C. The absolute pressure of the gas phase at which said contacting is carried out is preferably in the range of from 0.1 to 2.0 bar, preferably in the range of from 0.5 to 1.5 bar, more preferably in the range of from 0.8 to 1.1 bar. Therefore, it is preferred that the contacting of the compound of formula (II) with the solid porous catalyst comprising silica is carried out at a temperature of the gas phase in the range of from 300 to 400° C. and an absolute pressure of the gas phase in the range of from 0.8 to 1.1 bar.

Generally, it is conceivable that the gas phase which is brought into contact with the solid porous catalyst comprising silica consists of the gaseous compound of formula (II) and optionally a carrier gas which is described herein under. Preferably, the gas phase which is brought into contact with the solid porous catalyst comprising silica comprises the gaseous compound of formula (II), optionally a carrier gas, and a diluent.

Preferably, the comprises, more preferably consists of, one or more of optionally substituted aliphatic hydrocarbon, optionally aromatic hydrocarbon, ether, alkylnitrile, alkanol, water. More preferably, the diluent comprises, more preferably consists of, one or more of pentane, hexane, heptane, petroleum ether, cyclohexane, dichloromethane, trichloromethane, tetrachloromethane, benzene, toluene, xylene, chlorobenzene, dichlorobenzene, diethylether, methyl-tert-butylether, dibutylether, tetrahydrofuran, dioxane, acetonitrile, propionitrile, methanol, ethanol, water. More preferably, the diluent comprises, preferably consists of, one or more of diethylether, methyl-tert-butylether, tetrahydrofuran, acetonitrile, water. More preferably, the diluent comprises water. More preferably, at least 0.3 weight-%, preferably at least 1 weight-%, more preferably at least 10 weight-%, more preferably at least 50 weight-%, more preferably at least 99 weight-%, more preferably at least 99.9 weight-% of the diluent consist of water. More preferably, the diluent is water.

With regard to the amount of diluent used, no specific restrictions exist, and the weight ratio of the diluent relative to the compound of formula (II) can be varied in wide ranges. Preferably, prior to contacting the compound of formula (II) with the solid porous catalyst comprising silica, the weight ratio of the diluent relative to the compound of formula (II) is in the range of from 20:1 to 1:100, preferably in the range of from 10:1 to 1:10, more preferably in the range of from 5:1 to 1:1.

While it is generally conceivable that contacting the compound of formula (II) with the solid porous catalyst comprising silica is carried out in batch mode or in semicontinous mode, it is preferred that the contacting is carried out in continuous mode. According to this continuous mode, it is possible that the compound of formula (II), in gaseous form, and preferably the diluent, in gaseous form, are passed into a suitable reaction zone, such as a tubular reactor or the like which contains the solid porous catalyst comprising silica. Prior to passing the compound of formula (II), in gaseous form, and the diluent, in gaseous form, into the reaction zone, the compound of formula (II) and the diluent can be admixed with each other.

The reaction zone can be designed in all forms suitable for gas phase reactions. Usually, the reaction zone is a cylindrical or tubular reactor which is at least partially filled with the solid porous catalyst comprising silica. The solid catalyst can be arranged in the reaction as a fixed bed, as a fluidized bed, or as a packing. The reaction zone can be arranged horizontally or vertically wherein, in case the reaction is arranged vertically, the gas phase can be passed throughout the reaction zone in upstream mode or in downstream mode. Usually, for tubular reaction zones, the length of the reaction zone, i.e. the zone which is filled with the catalyst, relative to the internal diameter of the reaction zone, is at least 3:1, preferably in the range of from 3:1 to 100:1, more preferably in the range of from 5:1 to 10:1. The reaction zone is usually equipped with heating means such as electrical heating or induction heating. Preferably, an evaporation zone is arranged upstream of the reaction zone in which the compound of formula (II) and optionally the diluent are evaporated. If the reaction zone is comprised in a tubular reactor, it is possible, for example, that a first zone of the tubular reactor is designed as the evaporation zone and a downstream zone of the tubular reactor is the reaction zone comprising the solid catalyst.

For passing the compound of formula (II), in gaseous form, and the diluent, in gaseous form, into and through the reaction zone, a carrier gas can be employed. Therefore, the gas phase which is brought into contact with the solid porous catalyst comprising silica preferably comprises a carrier gas.

No specific restrictions exist with regard to the chemical nature of the carrier gas. Preferably, the carrier gas is a gas or a mixture of two or more gases which is inert with respect to the thermolysis reaction. The term "inert" as used in this context of the present invention relates to a gas or a mixture of two or more gases which does not have a negative influence on the thermolysis reaction. Preferably, the carrier gas comprises one or more of helium, argon, nitrogen, more preferably nitrogen. More preferably, the carrier gas is nitrogen, more preferably technical nitrogen having a nitrogen content of at least 99.5 volume-% and an oxygen content of at most 0.5 volume-%.

With regard to the amount of carrier gas used, no specific restrictions exist, and the volume ratio of the carrier gas relative to the compound of formula (II) can be varied in wide ranges. Preferably, prior to contacting the compound of formula (II) with the solid porous catalyst comprising silica, the volume ratio of the carrier gas relative to the compound of formula (II) in its gaseous form is in the range of from 1:1 to 20:1, preferably in the range of from 2:1 to 15:1, more preferably in the range of from 5:1 to 10:1.

With regard to the volume flow through the reaction zone comprising the solid porous catalyst comprising silica, it is preferred that the achieved catalyst load is at least 0.01 kg/kg/h. The catalyst load is defined as mass of the compound of formula (II) in kg per 1 kg of the catalyst material per 1 h. Preferably, the catalyst load is in the range of from 0.01 to 5 kg(compound of formula (II))/kg(catalyst)/h, more preferably in the range of from 0.02 to 2 kg(compound of formula (II))/kg(catalyst)/h, more preferably in the range of from 0.05 to 1 kg(compound of formula (II))/kg(catalyst)/h, more preferably in the range of from 0.1 to 0.5 kg(compound of formula (II))/kg(catalyst)/h.

From the thermolysis reaction of the present invention, a reaction mixture is obtained, preferably at the exit of the reaction zone comprising the solid porous catalyst comprising silica. Surprisingly, it was found that the use of the catalyst of the present invention leads to a very advantageous process in terms of the yield of the reaction with regard to the compound of formula (I). Even more surprisingly, it was found that the use of catalyst of the present invention leads to a very advantageous process in terms of the yield of the reaction with regard to the compound of formula (I-a)

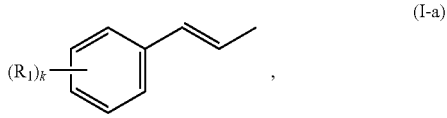

the trans-isomer of the compound of formula (I). Thus, it was found that the use the catalyst of the present invention leads to a very selective process with regard to the compound of formula (I-a), and thus to a reaction mixture exhibiting a very high molar ratio of the compound of formula (I-a) relative to the compound of formula (I-b)

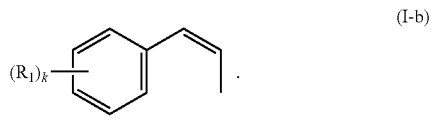

In particular in case the compound of formula (I) is a compound of formula

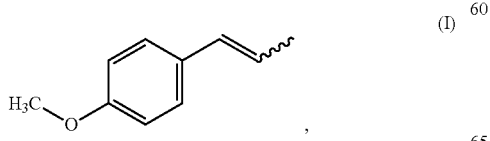

the trans-isomer is of particular commercial interest.

Therefore, the present invention also relates to the use of solid porous catalyst comprising silica, wherein the catalyst has a pore volume of at least 0.5 cm$^3$/g and an acidity characterized by an amount of adsorbed ammonia of at most 0.1 mmol/g as a catalyst for increasing the selectivity of solid catalyst gas-phase thermolysis of a compound of formula (II) with respect to the compound of formula (I-a).

Further, the present invention also relates to said reaction mixture which is directly obtained from contacting a compound of formula (II) in the gas phase with a solid porous catalyst comprising silica, said reaction mixture comprising a compound of formula (I) comprising a compound of formula formula (I-a) and optionally a compound of formula (I-b). The term "directly obtained" as used in this context of the present invention relates to a reaction mixture which is obtained at the exit of the reaction zone in which the contacting is carried out and which is not subjected to any further treatment such as separating the compound of formula (I-a) from the compound of formula (I-b). In said reaction mixture of the present invention, the molar amount of the compound of formula (I-a) relative to the molar amount of the converted compound of formula (II), optionally—in case a mixture of the compounds of formulas (II), (II-b) and (II-c) is used as starting material—relative to the sum of the molar amounts of the converted compounds of formulas (II), (II-b) and (II-c), is at least 0.3, more preferably at least 0.4, more preferably at least 0.5, more preferably at least 0.6. Since according to the present invention, the conversion of the compound of formula (II) is high, the yield with respect to the compound of formula (I) is high, and also the selectivity towards the compound of formula (I-a) is high, this reaction mixture allows for a simple and efficient work-up, for example for separating the compound of formula (I) and/or (I-a) from the reaction mixture.

After having left the reaction zone, the reaction mixture is preferably cooled, for example in a cooler arranged directly downstream the reaction zone. The cooling is preferably carried out so that the cooled reaction mixture has a temperature in the range of from 0 to 40° C., preferably in the range of from 0 to 35° C., more preferably in the range of from 0 to 30° C., more preferably in the range of from 0 to 25° C., more preferably in the range of from 0 to 20° C., more preferably in the range of from 0 to 15° C., more preferably in the range of from 0 to 10° C. Suitable coolers include, for example, intensive coolers and cold traps.

The valuable products contained in the thus cooled mixture can be separated from the mixture according to generally known methods, including extraction, distillation, crystallization or chromatographic isolation. Therefore, the present invention also relates to the process as described above, wherein the compound of formula (I) comprises a compound of formula (I-a)

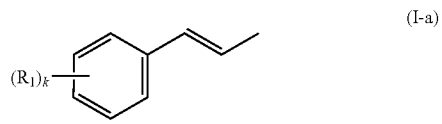

and a compound of formula (I-b)

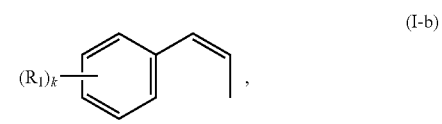

said process further comprising separating the compound of formula (I-a) from the compound of formula (I-b).

Depending on the chemical nature of the starting material, the mixture obtained from the thermolysis reaction contains a mixture of the cis-isomer and the trans-isomer or also a mixture of regioisomers comprising ortho-, meta- and/or para-substituted compounds. The separation of the individual isomers is preferably carried out by fractional distillation or chromatographic isolation.

Preferably, the mixture is subjected to distillation wherein distillation columns—equipped, for example, with bubble-cup trays, sieve plates, sieve trays, packings—or rotating-strip columns or evaporators such as thin film evaporator, falling film evaporator, forced circulation evaporator, sambay evaporator and the like. More preferably, distillation columns are used, in particular rotating-strip columns.

The present invention is further illustrated by the following embodiments and combinations of embodiments as indicated by the respective dependencies and back-references.

1. A process for preparing a compound of formula (I)

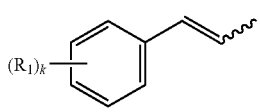
(I)

comprising contacting a compound of formula (II)

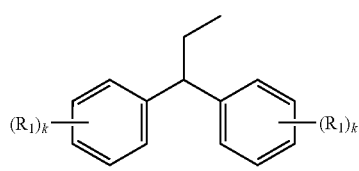
(II)

in the gas phase with a solid porous catalyst comprising silica, wherein
k is, independently from each other, 0, 1, 2 or 3;
$R_1$ is, independently from each other, hydroxy, $C_1$-$C_6$ alkoxy, di($C_1$-$C_6$-alkyl) aminyl;
wherein the catalyst has a pore volume of at least 0.5 cm$^3$/g as determined by Hg porosimetry according to DIN 66133, and an acidity characterized by an amount of adsorbed ammonia of at most 0.1 mmol/g(catalyst) as determined by NH$_3$-TPD, in particular as determined by NH$_3$-TPD at an ammonia adsorption at 100° C. and an ammonia desorption at 600° C., in particular an ammonia desorption achieved by heating from 100° C. to 600° C. at a heating rate of 10 K/min and holding for 30 min under a He flow of 30 cm$^3$/min, as described in Reference Example 2.1 herein.

2. The process of embodiment 1, wherein the catalyst has a pore volume in the range of from 0.5 to 2.0 cm$^3$/g.

3. The process of embodiment 1 or 2, wherein the catalyst has a pore volume in the range of from 0.5 to 1.5 cm$^3$/g, preferably in the range of from 0.6 to 1.2 cm$^3$/g, preferably in the range of from 0.7 to 1.1 cm$^3$/g.

4. The process of any one of embodiments 1 to 3, wherein the catalyst has a pore volume in the range of from 0.8 to 1.0 cm$^3$/g.

5. The process of any one of embodiments 1 to 4, wherein the catalyst has an acidity characterized by an amount of adsorbed ammonia in the range of from 0.01 to 0.09 mmol/g(catalyst).

6. The process of any one of embodiments 1 to 5, wherein the catalyst has an acidity characterized by an amount of adsorbed ammonia in the range of from 0.01 to 0.08 mmol/g(catalyst), preferably in the range of from 0.01 to 0.07 mmol/g(catalyst), more preferably in the range of from 0.01 to 0.06 mmol/g(catalyst).

7. The process of any one of embodiments 1 to 6, wherein the catalyst has an acidity characterized by an amount of adsorbed ammonia in the range of from 0.02 to 0.05 mmol/g(catalyst).

8. The process of any one of embodiments 1 to 7, wherein the catalyst has a pore volume in the range of from 0.5 to 2.0 cm$^3$/g and an acidity characterized by an amount of adsorbed ammonia in the range of from 0.01 to 0.09 mmol/g(catalyst).

9. The process of any one of embodiments 1 to 8, wherein the catalyst has a pore volume in the range of from 0.5 to 1.5 cm$^3$/g and an acidity characterized by an amount of adsorbed ammonia in the range of from 0.01 to 0.08 mmol/g(catalyst), preferably a pore volume in the range of from 0.6 to 1.2 cm$^3$/g and an acidity characterized by an amount of adsorbed ammonia in the range of from 0.01 to 0.07 mmol/g(catalyst), more preferably a pore volume in the range of from 0.7 to 1.1 cm$^3$/g and an acidity characterized by an amount of adsorbed ammonia in the range of from 0.01 to 0.06 mmol/g(catalyst).

10. The process of any one of embodiments 1 to 9, wherein the catalyst has a pore volume in the range of from 0.8 to 1.0 cm$^3$/g and an acidity characterized by an amount of adsorbed ammonia in the range of from 0.02 to 0.05 mmol/g(catalyst).

11. The process of any one of embodiments 1 to 10, wherein the catalyst has an acidity characterized in that, as determined by NH$_3$-TPD, in particular as determined by NH$_3$-TPD at an ammonia adsorption at 100° C. and an ammonia desorption at 600° C., in particular an ammonia desorption achieved by heating from 100° C. to 600° C. at a heating rate of 10 K/min and holding for 30 min under a He flow of 30 cm$^3$/min, as described in Reference Example 2.1 herein, at least 95%, preferably at least 99%, more preferably at least 99.9% of the ammonia is desorbed at temperatures of at most 250° C., preferably of at most 225° C., more preferably of at most 200° C.

12. The process of any one of embodiments 1 to 11, wherein at least 75 weight-%, preferably at least 90 weight-%, more preferably at least 95 weight-% of the catalyst consist of silica, more preferably at least 99 weight-% of the catalyst consist of silica.

13. The process of any one of embodiments 1 to 12, wherein at least 99.5 weight-% of the catalyst consist of silica.

14. The process of any one of embodiments 1 to 13, preferably of any one of embodiments 11 to 13, wherein the catalyst comprises one or more alkali metal oxides, preferably sodium oxide.

15. The process of embodiment 14, wherein the catalyst comprises the one or more alkali metal oxides, preferably the sodium oxide, in an amount of at most 0.5 weight-%, preferably in an amount in the range of from 0.05 to 0.4 weight-%, more preferably in the range of from 0.1 to 0.3 weight-%, based on the weight of the catalyst.

16. The process of any one of embodiments 1 to 15, wherein at least 75 weight-% of the catalyst consist of silica and wherein the catalyst has a pore volume in the range of from 0.5 to 2.0 cm³/g and an acidity characterized by an amount of adsorbed ammonia in the range of from 0.01 to 0.09 mmol/g(catalyst).

17. The process of any one of embodiments 1 to 16, wherein at least 99.5 weight-% of the catalyst consist of silica and wherein the catalyst has a pore volume in the range of from 0.8 to 1.0 cm³/g and an acidity characterized by an amount of adsorbed ammonia in the range of from 0.02 to 0.05 mmol/g(catalyst).

18. A process for preparing a compound of formula (I)

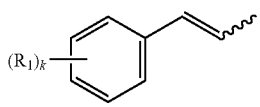

comprising contacting a compound of formula (II)

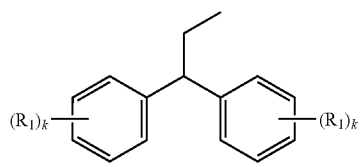

in the gas phase with a solid porous catalyst comprising silica, wherein
k is, independently from each other, 0, 1, 2 or 3;
$R_1$ is, independently from each other, hydroxy, $C_1$-$C_6$ alkoxy, di($C_1$-$C_6$-alkyl) aminyl;
wherein at least 75 weight-% of the catalyst consist of silica and wherein the catalyst has a pore volume in the range of from 0.5 to 2.0 cm³/g and an acidity characterized by an amount of adsorbed ammonia in the range of from 0.01 to 0.09 mmol/g(catalyst), preferably wherein at least 99.5 weight-% of the catalyst consist of silica and wherein the catalyst has a pore volume in the range of from 0.8 to 1.0 cm³/g and an acidity characterized by an amount of adsorbed ammonia in the range of from 0.02 to 0.05 mmol/g(catalyst).

19. The process of any one of embodiments 1 to 18, preferably of embodiment 16 or 17, wherein the catalyst is in the form of moldings, preferably in the form of strands, more preferably in the form of strands having an essentially circular cross section.

20. The process of embodiment 19, wherein the cross section has a diameter in the range of from 1 to 5 mm, preferably in the range of from 1.5 to 4 mm.

21. The process of any one of embodiments 1 to 20, wherein $C_1$-$C_6$ alkoxy includes methoxy, ethoxy, n-propoxy, 1-methylethoxy, n-butoxy, 1-methylpropoxy, 2-methylpropoxy, 1,1-dimethylethoxy, n-pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, 1-ethyl-2-methylpropoxy.

22. The process of any one of embodiments 1 to 21, wherein in di($C_1$-$C_6$-alkyl) aminyl, the $C_1$-$C_6$-alkyl includes methyl, ethyl, propyl, isopropyl, n-butyl, isobutyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl.

23. The process of any one of embodiments 1 to 22, wherein $R_1$ is, independently from each other, hydroxy, $C_1$-$C_4$-alkoxy, di($C_1$-$C_3$-alkyl)aminyl, preferably hydroxy, $C_1$-$C_3$-alkoxy, di($C_1$-$C_3$-alkyl)-aminyl, more preferably hydroxy, $C_1$-$C_3$-alkoxy, more preferably hydroxy, $C_1$-$C_2$-alkoxy.

24. The process of any one of embodiments 1 to 23, wherein the compound of formula (I) is a compound of formula

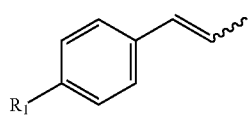

and the compound of formula (II) is a compound of formula

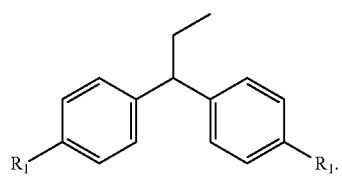

25. The process of any one of embodiments 1 to 24, preferably of embodiment 24, wherein $R_1$ is hydroxy or methoxy.

26. The process of any one of embodiments 1 to 25, wherein the compound of formula (I) is a compound of formula

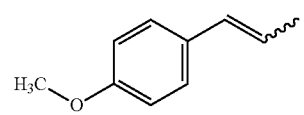

and the compound of formula (II) is a compound of formula

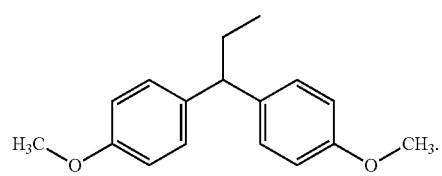

27. The process of embodiment 26, wherein, prior to the contacting with the solid porous catalyst comprising silica, the gas phase comprises, in addition to the compound of formula (II), the compound of formula (II-b)

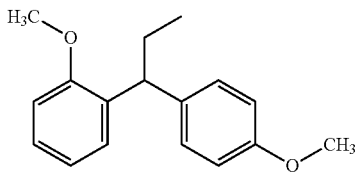

and the compound of formula (II-c)

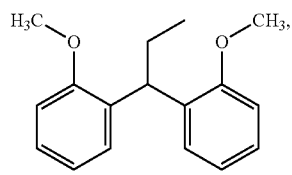

wherein the molar ratio of the compound of formula (II) relative to the sum of the compound of formula (II), the compound of formula (II-b) and the compound of formula (II-c) is preferably in the range of from 65 to 75%, the molar ratio of the compound of formula (II-b) relative to the sum of the compound of formula (II), the compound of formula (II-b) and the compound of formula (II-c) is preferably in the range of from 25 to 30%, and the molar ratio of the compound of formula (II-c) relative to the sum of the compound of formula (II), the compound of formula (II-b) and the compound of formula (II-c) is preferably in the range of from 1 to 5% wherein more preferably, these molar ratios add up to 100%.

28. A process for preparing a compound of formula (I)

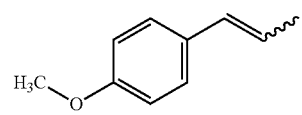

comprising contacting a compound of formula (II)

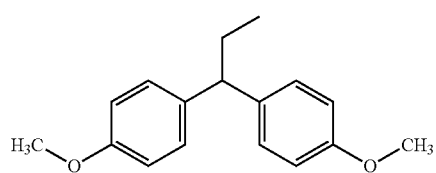

in the gas phase with a solid porous catalyst comprising silica,
wherein at least 75 weight-% of the catalyst consist of silica and wherein the catalyst has a pore volume in the range of from 0.5 to 2.0 cm³/g and an acidity characterized by an amount of adsorbed ammonia in the range of from 0.01 to 0.09 mmol/g(catalyst), preferably wherein at least 99.5 weight-% of the catalyst consist of silica and wherein the catalyst has a pore volume in the range of from 0.8 to 1.0 cm³/g and an acidity characterized by an amount of adsorbed ammonia in the range of from 0.02 to 0.05 mmol/g(catalyst).

29. The process of any one of embodiments 1 to 28, wherein contacting the compound of formula (II) with the solid porous catalyst is carried out under thermolytic condition, wherein contacting the compound of formula (II) with the solid porous catalyst is preferably carried out at a temperature of the gas phase in the range of from 250 to 650° C., more preferably in the range of from 260 to 600° C., more preferably in the range of from 270 to 550° C., more preferably in the range of from 280 to 500° C., more preferably in the range of from 290 to 450° C.

30. The process of any one of embodiments 1 to 29, wherein contacting the compound of formula (II) with the solid porous catalyst is carried out at a temperature of the gas phase in the range of from 300 to 400° C.

31. The process of any one of embodiments 1 to 30, wherein contacting the compound of formula (II) with the solid porous catalyst is carried out at an absolute pressure of the gas phase in the range of from 0.1 to 2.0 bar, preferably in the range of from 0.5 to 1.5 bar.

32. The process of any one of embodiments 1 to 31, wherein contacting the compound of formula (II) with the solid porous catalyst is carried out at an absolute pressure of the gas phase in the range of from 0.8 to 1.1 bar.

33. The process of any one of embodiments 1 to 32, wherein contacting the compound of formula (II) with the solid porous catalyst is carried out in the presence of a diluent.

34. The process of embodiment 33, wherein the diluent comprises, preferably consists of, one or more of optionally substituted aliphatic hydrocarbon, optionally aromatic hydrocarbon, ether, alkylnitrile, alkanol, water.

35. The process of embodiment 33 or 34, wherein the diluent comprises, preferably consists of, one or more of pentane, hexane, heptane, petroleum ether, cyclohexane, dichloromethane, trichloromethane, tetrachloromethane, benzene, toluene, xylene, chlorobenzene, dichlorobenzene, diethylether, methyl-tert-butylether, dibutylether, tetrahydrofuran, dioxane, acetonitrile, propionitrile, methanol, ethanol, water.

36. The process of any one of embodiments 33 to 35, wherein the diluent comprises, preferably consists of, one or more of diethylether, methyl-tert-butylether, tetrahydrofuran, acetonitrile, water.

37. The process of any one of embodiments 33 to 36, wherein at least 0.3 weight-%, preferably at least 1 weight-%, more preferably at least 10 weight-%, more preferably at least 50 weight-%, more preferably at least 99 weight-%, more preferably at least 99.9 weight-% of the diluent consist of water, wherein more preferably, the diluent is water.

38. The process of any one of embodiments 1 to 37, wherein prior to contacting the compound of formula (II) with the solid porous catalyst, the weight ratio of the diluent relative to the compound of formula (II) is in the range of from 20:1 to 1:100, preferably in the range of from 10:1 to 1:10, more preferably in the range of from 5:1 to 1:1.

39. The process of any one of embodiments 1 to 38, being carried out in continuous mode.

40. The process of any one of embodiment 1 to 39, preferably 39, wherein contacting the compound of formula (II) in the gas phase with the solid porous catalyst is carried out in a reaction zone comprising the solid porous catalyst, the process comprising passing, preferably continuously passing, the gas phase comprising the compound of formula (II) and optionally the diluent into and through the reaction zone comprising the solid catalyst.

41. The process of any one of embodiments 1 to 40, wherein the gas phase further comprises a carrier gas.
42. The process of embodiment 41, wherein the carrier gas comprises one or more of helium, argon, nitrogen, preferably nitrogen, wherein more preferably, the carrier gas is nitrogen, more preferably technical nitrogen.
43. The process of embodiment 41 or 42, wherein prior to contacting the compound of formula (II) with the solid porous catalyst, the volume ratio of the carrier gas relative to the compound of formula (II) in its gaseous form is in the range of from 1:1 to 20:1, preferably in the range of from 2:1 to 15:1, more preferably in the range of from 5:1 to 10:1.
44. The process of any one of embodiments 1 to 43, wherein contacting the compound of formula (II) with the solid porous catalyst is carried out at a catalyst load in the range of from 0.01 to 5 kg(compound of formula (II))/kg(catalyst)/h, preferably in the range of from 0.02 to 2 kg(compound of formula (II))/kg(catalyst)/h, more preferably in the range of from 0.05 to 1 kg(compound of formula (II))/kg(catalyst)/h, more preferably in the range of from 0.1 to 0.5 kg(compound of formula (II))/kg(catalyst)/h.
45. The process of any one of embodiments 1 to 44, further comprising cooling the reaction mixture to a temperature in the range of from 0 to 40° C., preferably in the range of from 0 to 20° C., more preferably in the range of from 0 to 10° C.
46. The process of any one of embodiments 1 to 45, wherein the compound of formula (I) comprises a compound of formula (I-a)

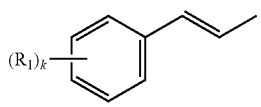
(I-a)

and a compound of formula (I-b)

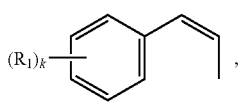
(I-b)

said process further comprising separating the compound of formula (I-a) from the compound of formula (I-b).

47. The process of embodiment 46, preferably insofar as embodiment 46 is dependent on embodiment 27, wherein the compound of formula (I) is a compound of formula

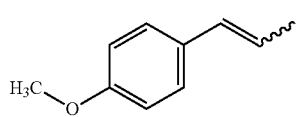
(I)

and the compound of formula (II) is a compound of formula

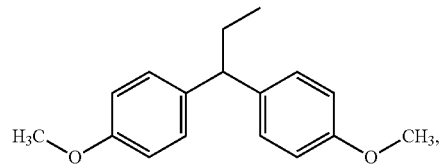
(II)

said compound of formula (I) comprising a compound of formula (I-a)

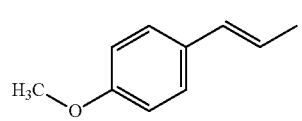
(I-a)

and a compound of formula (I-b)

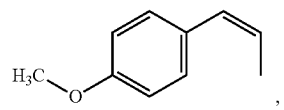
(I-b)

said process comprising separating the compound of formula (I-a) from the compound of formula (I-b).

48. A process for preparing a compound of formula (I)

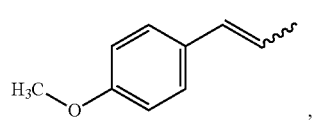
(I)

comprising contacting a compound of formula (II)

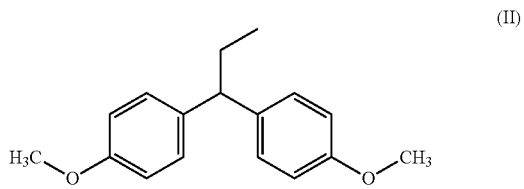
(II)

in the gas phase with a solid porous catalyst comprising silica,
wherein at least 75 weight-% of the catalyst consist of silica and wherein the catalyst has a pore volume in the range of from 0.5 to 2.0 cm³/g and an acidity characterized by an amount of adsorbed ammonia in the range of from 0.01 to 0.09 mmol/g(catalyst), preferably wherein at least 99.5 weight-% of the catalyst consist of silica and wherein the catalyst has a pore volume in the range of from 0.8 to 1.0 cm³/g and an acidity characterized by an amount of adsorbed ammonia in the range of from 0.02 to 0.05 mmol/g(catalyst), obtaining a compound of formula (I)

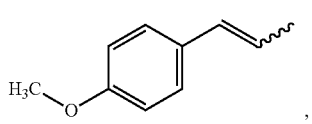 (I)

said compound of formula (I) comprising the compound of formula (I-a) and a compound of formula (I-b)

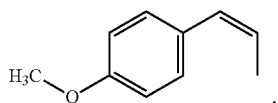 (I-b)

said process comprising separating the compound of formula (I-a) from the compound of formula (I-b).

49. The process of any one of embodiments 46 to 48, wherein separating the compound of formula (I-a) from the compound of formula (I-b) and optionally from the compound of formula (I-c) and optionally from the compound of formula (I-d) comprises subjecting the compound of formula (I) to distillation and/or chromatography, preferably distillation.

50. A reaction mixture, obtainable or obtained from contacting a compound of formula (II)

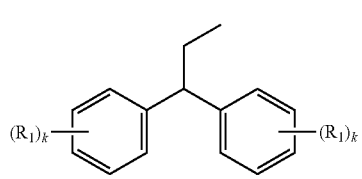 (II)

in the gas phase with a solid porous catalyst comprising silica, wherein k is, independently from each other, 0, 1, 2 or 3;

$R_1$ is, independently from each other, hydroxy, $C_1$-$C_6$ alkoxy, di($C_1$-$C_6$-alkyl) aminyl;

wherein the catalyst has a pore volume of at least 0.5 cm³/g as determined by Hg porosimetry according to DIN 66133, and an acidity characterized by an amount of adsorbed ammonia of at most 0.1 mmol/g(catalyst) as determined by $NH_3$-TPD, in particular as determined by $NH_3$-TPD at an ammonia adsorption at 100° C. and an ammonia desorption at 600° C., in particular an ammonia desorption achieved by heating from 100° C. to 600° C. at a heating rate of 10 K/min and holding for 30 min under a He flow of 30 cm³/min, as described in Reference Example 2.1 herein;

said reaction mixture preferably being obtainable or obtained by a process according to any one of embodiments 1 to 44, said reaction mixture comprising a compound of formula (I)

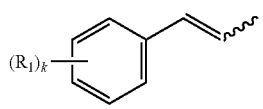 (I)

comprising a compound of formula formula (I-a)

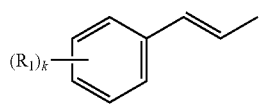 (I-a)

and a compound of formula (kb)

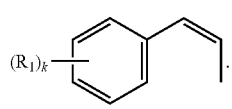 (I-b)

51. The reaction mixture of embodiment 50, wherein said process does not comprise separating the compound of formula (I-a) from the compound of formula (I-b).

52. The reaction mixture of embodiment 50 or 51, wherein the compound of formula (I) is

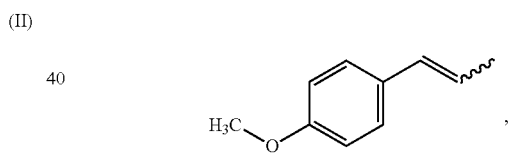 (I)

the compound of formula (II) is

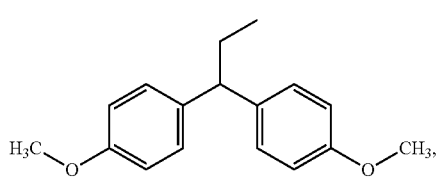 (II)

the compound of formula (I-a) is

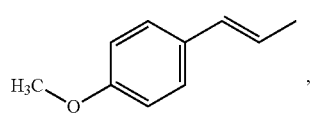 (I-a)

and the compound of formula (I-b) is

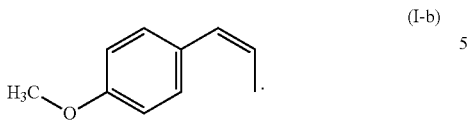

53. The reaction mixture of any one of embodiments 50 to 52, wherein the molar ratio of the compound of formula (I-a) relative to the molar amount of the converted compound of formula (II), optionally relative to the sum of the molar amounts of the converted compounds of formulas (II), (II-b) and (II-c), is at least 0.3, more preferably at least 0.4, more preferably at least 0.5, more preferably at least 0.6

54. Use of a solid porous catalyst comprising silica, wherein the catalyst has a pore volume of at least 0.5 cm$^3$/g as determined by Hg porosimetry according to DIN 66133, and an acidity characterized by an amount of adsorbed ammonia of at most 0.1 mmol/g(catalyst) as determined by NH$_3$-TPD, in particular as determined by NH$_3$-TPD at an ammonia adsorption at 100° C. and an ammonia desorption at 600° C., in particular an ammonia desorption achieved by heating from 100° C. to 600° C. at a heating rate of 10 K/min and holding for 30 min under a He flow of 30 cm$^3$/min, as described in Reference Example 2.1 herein, as a catalyst for increasing the selectivity of solid catalyst gas-phase thermolysis of a compound of formula (II)

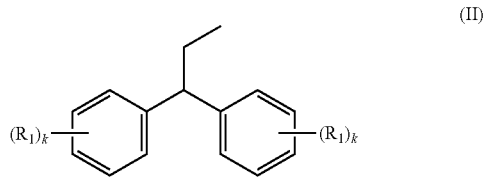

with respect to the compound of formula (I-a)

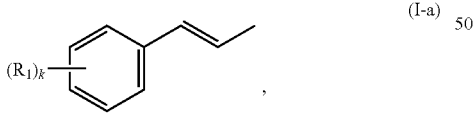

wherein
k is, independently from each other, 0, 1, 2 or 3;
R$_1$ is, independently from each other, hydroxy, C$_1$-C$_6$ alkoxy, di(C$_1$-C$_6$-alkyl) aminyl.

55. The use of embodiment 54, wherein the solid porous catalyst comprising silica is as defined in any one of embodiments 2 to 20, preferably as defined in embodiment 16 or 17, more preferably as defined in embodiment 17, more preferably as defined in embodiments 19 and 20 insofar embodiments 19 and 20 are dependent of embodiment 16 or 17, preferably 17.

56. The use of embodiment 54 or 55, wherein the compound of formula (II) is

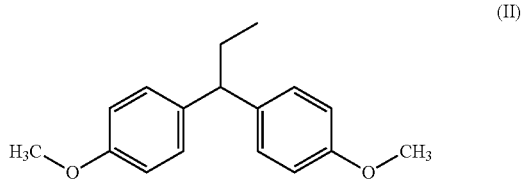

and the compound of formula (I-a) is

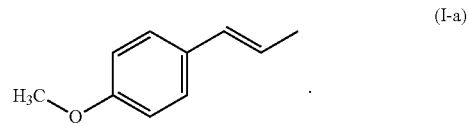

57. A method of increasing the selectivity of solid catalyst gas-phase thermolysis of a compound of formula (II)

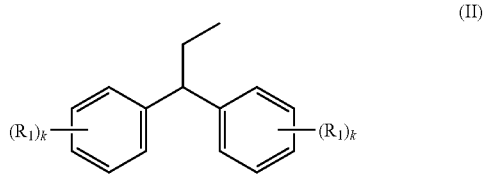

with respect to the compound of formula (I-a)

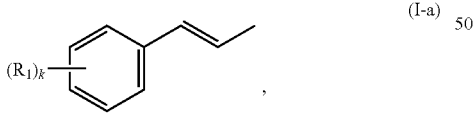

wherein
k is, independently from each other, 0, 1, 2 or 3;
R$_1$ is, independently from each other, hydroxy, C$_1$-C$_6$ alkoxy, di(C$_1$-C$_6$-alkyl) aminyl,
said method comprising employing a catalyst comprising silica, wherein the catalyst has a pore volume of at least 0.5 cm$^3$/g as determined by Hg porosimetry according to DIN 66133, and an acidity characterized by an amount of adsorbed ammonia of at most 0.1 mmol/g (catalyst) as determined by NH$_3$-TPD, in particular as determined by NH$_3$-TPD at an ammonia adsorption at 100° C. and an ammonia desorption at 600° C., in particular an ammonia desorption achieved by heating from 100° C. to 600° C. at a heating rate of 10 K/min and holding for 30 min under a He flow of 30 cm$^3$/min, as described in Reference Example 2.1 herein.

58. The method of embodiment 47, wherein the solid porous catalyst comprising silica is as defined in any one of embodiments 2 to 20, preferably as defined in embodiment 16 or 17, more preferably as defined in embodiment 17, more preferably as defined in embodiments 19 and 20 insofar embodiments 19 and 20 are dependent of embodiment 16 or 17, preferably 17.

59. The method of embodiment 57 or 58, wherein the compound of formula (II) is

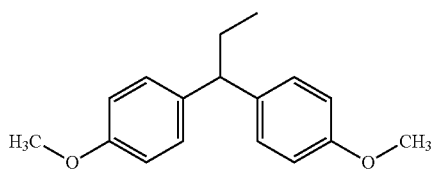
(II)

and the compound of formula (I-a) is

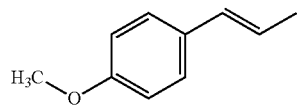
(I-a)

60. Use of a silica having a pore volume of at least 0.5 cm³/g as determined by Hg porosimetry according to DIN 66133, and having an acidity characterized by an amount of adsorbed ammonia of at most 0.1 mmol/g(catalyst) as determined by $NH_3$-TPD, in particular as determined by $NH_3$-TPD at an ammonia adsorption at 100° C. and an ammonia desorption at 600° C., in particular an ammonia desorption achieved by heating from 100° C. to 600° C. at a heating rate of 10 K/min and holding for 30 min under a He flow of 30 cm³/min, as described in Reference Example 2.1 herein, for preparing a compound of formula (I)

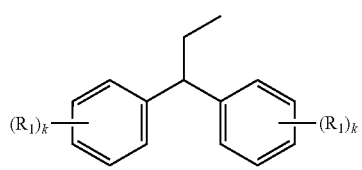
(I)

preferably for increasing the selectivity of solid catalyst gas-phase thermolysis of a compound of formula (II)

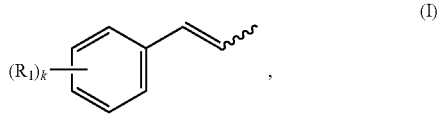
(II)

with respect to the compound of formula (I-a)

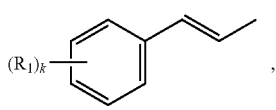
(I-a)

wherein
k is, independently from each other, 0, 1, 2 or 3;
$R_1$ is, independently from each other, hydroxy, $C_1$-$C_6$ alkoxy, di($C_1$-$C_6$-alkyl) aminyl, wherein the compound of formula (I) is preferably a compound

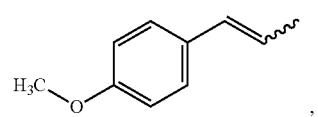
(I)

the compound of formula (I-a) is preferably a compound

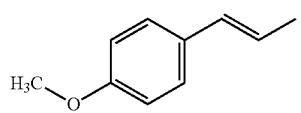
(I-a)

the compound of formula (II) is preferably a compound

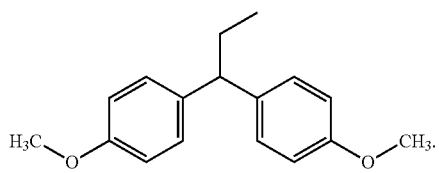
(II)

The present invention is further illustrated by the following reference examples, examples and comparative examples.

EXAMPLES

Reference Example 1: Catalysts

Reference Example 1.1: Catalyst According to the Invention

About 100 weight-% of this catalyst consisted silica. The catalyst had a pore volume, determined as described in Reference Example 2.2 herein, of 0.86 cm³/g and an acidity, characterized by an amount of adsorbed ammonia of 0.03 mmol/g, determined as described in Reference Example 2.1 herein. The catalyst was in the form of extrudates (strands) having an essentially circular cross-section with a diameter in the range of from 2.4 mm. Such a catalyst is, for example, commercially available as "D11-10" from BASF SE.

Reference Example 1.2: Catalyst (Comparative)

This catalyst consisted of silica and phosphorous oxide ($P_2O_5$). The weight ratio of silica relative to phosphorous oxide was 4:1. The catalyst had a pore volume, determined as described in Reference Example 2.2 herein, of 0.30 cm³/g and an acidity, characterized by an amount of adsorbed ammonia of 0.1 mmol/g, determined as described in Reference Example 2.1 herein. The catalyst was in the form of extrudates (strands) having an essentially circular cross-section with a diameter of 1.5 mm. The catalyst was prepared by impregnating the strands according to Reference Example 2.1 hereinabove with phosphoric acid and subsequent drying.

Reference Example 1.3: Catalyst (Comparative)

About 100 weight-% of this catalyst consisted silica and alumina. The weight ratio of silica relative to alumina was about 1:4. The catalyst had a pore volume, determined as described in Reference Example 2.2 herein, of 0.58 cm³/g and an acidity, characterized by an amount of adsorbed ammonia of 0.5 mmol/g, determined as described in Reference Example 2.1 herein. The catalyst was in the form of extrudates (strands) having an essentially circular cross-section with a diameter of 2 mm. Such a catalyst is, for example, commercially available as "D10-10" from BASF SE.

Reference Example 1.4: Catalyst (Comparative)

This catalyst was a mesoporous silica of which 100 weight-% consisted of silica. The catalyst had a pore volume, determined as described in Reference Example 2.2 herein, of 0.40 cm³/g and an estimated acidity, characterized by an amount of adsorbed ammonia of 0.03 mmol/g, determined as described in Reference Example 2.1 herein. The catalyst was in the form of extrudates (strands) having an essentially circular cross-section with a diameter of 2 mm.

The catalyst was prepared by mixing 31.3 g tetraethyl orthosilicate (TEOS), 7.5 g polymer, 3.75 ml hydrochloric acid (32 weight-% in water) and 29.3 g water for 15 min. At a temperature of 60° C., the ethanol formed was distilled off, and within 10 min, a dry powder was formed which was then cooled to room temperature, dried overnight at 120° C., and calcined at a temperature of 550° C. for 5 h. The polymer used consisted of 90 weight-% methylmethacrylate, 5 weight-% butanedioldiacrylate, and 5 weight-% dimethylaminoethyl methacrylate quaternized with diethyl sulfate ("Quat 311").

The powder was extruded to obtain strands according to the following method: 145.5 g of the powder was admixed with 19.14 Ludox® AS-40 and 7.28 g Walocel® (Wolf Walsrode AG) for 10 min by kneading. Then, 29.1 g NH$_4$OH and 125 ml de-ionized water were added, and the resulting mixture was kneaded. Then, 2.9 g Zusoplast PS1 were added, and the resulting mixture was kneaded. The resulting mass was extruded to obtain strands having an essentially circular cross-section of a diameter of 2 mm. The strands were dried at 120° C. for 6 h in air and then calcined at 500° C. for 5 h in air.

Reference Example 2: Determination of Parameters

Reference Example 2.1: NH$_3$-TPD

The temperature-programmed desorption of ammonia (NH$_3$-TPD) was conducted in an automated chemisorption analysis unit (Micromeritics AutoChem II 2920) having a thermal conductivity detector. Continuous analysis of the desorbed species was accomplished using an online mass spectrometer (OmniStar QMG200 from Pfeiffer Vacuum). The sample (0.1 g) was introduced into a quartz tube and analyzed using the program described below. The temperature was measured by means of an Ni/Cr/Ni thermocouple immediately above the sample in the quartz tube. For the analyses, He of purity 5.0 was used. Before any measurement, a blank sample was analyzed for calibration.

1. Preparation: Commencement of recording; one measurement per second. Wait for 10 minutes at 25° C. and a He flow rate of 30 cm³/min (room temperature (about 25° C.) and 1 atm); heat up to 600° C. at a heating rate of 20 K/min; hold for 10 minutes. Cool down under a He flow (30 cm³/min) to 100° C. at a cooling rate of 20 K/min (furnace ramp temperature); Cool down under a He flow (30 cm³/min) to 100° C. at a cooling rate of 3 K/min (sample ramp temperature).
2. Saturation with NH$_3$: Commencement of recording; one measurement per second. Change the gas flow to a mixture of 10% NH$_3$ in He (75 cm³/min; 100° C. and 1 atm) at 100° C.; hold for 30 minutes.
3. Removal of the excess: Commencement of recording; one measurement per second. Change the gas flow to a He flow of 75 cm³/min (100° C. and 1 atm) at 100° C.; hold for 60 minutes.
4. NH$_3$-TPD: Commencement of recording; one measurement per second. Heat up under a He flow (flow rate: 30 cm³/min) to 600° C. at a heating rate of 10 K/min; hold for 30 minutes.
5. End of measurement.

Desorbed ammonia was measured by means of the online mass spectrometer, which demonstrates that the signal from the thermal conductivity detector was caused by desorbed ammonia. This involved utilizing the m/z=16 signal from ammonia in order to monitor the desorption of the ammonia. The amount of ammonia adsorbed (mmol/g of sample) was ascertained by means of the Micromeritics software through integration of the TPD signal with a horizontal baseline.

Reference Example 2.2: Pore Volume

The pore volumes were determined via Hg porosimetry according to DIN 66133.

Reference Example 2.3: BET Specific Surface Area

The BET specific surface area values were determined via nitrogen adsorption at 77 K according to DIN 66131.

Example 1: Preparing a Compound of Formula (I) (Anethole) Starting from a Compound of Formula (II) (1,1-bis(4-Methoxyphenyl)Propane)

The first zone (15 cm) of a gas phase oven, equipped with electrical heating means and having an inner diameter of 4 cm, was filled with quartz rings. The downstream zone (20 cm) was then filled with catalyst strands according to the Reference Examples 1.1 to 1.4. The first 15 cm filled with quartz rings was used as evaporating zone for the dimer and the diluent thereof (water). (The term "dimer" as used in this context refers to a mixture consisting of 70 mol-% 1,1-bis (4-methoxyphenyl)propane, 28 mol-% 1-(4-methoxyphenyl)-1-(2-methoxyphenyl) propane, and 2 mol-% 1,1-bis(2-methoxyphenyl)propane.) The weight ratio of 1,1-bis(4-methoxyphenyl)-propane relative to the water introduced into the reactor was as indicated below in Table 1. The dimer and the water were introduced into the evaporation zone as separate streams. As carrier gas, technical nitrogen was used. The volume ratio of the carrier gas relative to the (gaseous) dimer propane was as indicated below in Table 1. The thermolytic reaction was carried out at a temperature of the gas phase of 350° C. and a catalyst loading of 0.2 kg(dimer)/kg(catalyst)/h. The reaction mixture was condensed in a downstream cooling apparatus at a temperature of 5° C. The water was separated by phase separation, and the resulting organic phase was analyzed by gas chromatography.

The results obtained are given in Table 1 below:

TABLE 1

Results according to Example 1

| Catalyst (ref. ex. #) | Pore vol./cm$^3$/g | NH$_3$TPD/ mmol/g [1] | BET surface area/m$^2$/g | Dimer [2]/ g/h // H$_2$O/ g/h | Conv.[3]/ % | Select. comp. (I) [4] | Select. comp. (I-a) [5] |
|---|---|---|---|---|---|---|---|
| 1.1 | 0.86 | 0.03 | 160 | 6.4 // 18.7 | 60.8 | 92.0 | 61.0 |
| 1.2 | 0.30 | 0.1 | 20 | 6.6 // 19.4 | 18.6 | 76.5 | 56.4 |
| 1.3 | 0.58 | 0.5 | 205 | 6.6 // 19.8 | 49.3 | 25.0 | 15.1 |
| 1.4 | 0.40 | 0.03 [6] | 495 | 3.6 // 10.2 | 9.5 | 4.5 | 3.1 |

[1] mmol(NH$_3$)/g(catalyst).
[2] Dimer: 1,1-bis(4-methoxyphenyl)propane; see definition above.
[3] Conversion of dimer.
[4] Selectivity (I) is defined as the sum of the molar amounts of the compounds of formula (I-a) and the para-substituted cis-isomer of formula (I-b), divided by the molar amount of converted dimer (1,1-bis(4-methoxyphenyl)propane plus 1-(4-methoxyphenyl)-1-(2-methoxy-phenyl)propane plus 1,1-bis(2-methoxyphenyl)propane).
[5] Selectivity (I-a) is defined as the molar amount of the compound of formula (I-a) divided by the molar amount of converted dimer (1,1-bis(4-methoxyphenyl)propane plus 1-(4-methoxy-phenyl)-1-(2-methoxyphenyl)propane plus 1,1-bis(2-methoxyphenyl)propane).
[6] Estimated value.

Results

From the examples, it can be seen that a porous catalyst comprising silica, having a pore volume of at least 0.5 cm$^3$/g and an acidity of at most 0.1 mmol/g results to very advantageous results in that the highest conversion of the starting material, the highest selectivity with regard to the compound of formula (I) and the highest selectivity with regard to the compound of formula (I-a) is obtained. Therefore, at an identical catalyst load during the continuous process, the catalyst according to the invention allows to increase both the conversion and the selectivity compared to all other catalysts tested and, therefore, is an ideal catalyst, in particular for producing the compound of formula (I-a), in particular trans-anethole, on a commercial scale.

CITED PRIOR ART

CN 102491884 A
SU 261380
SU 355144
Maslozhirovaya Promyshlennost (1974), volume 9, pages 29-30
CN 103058835 A
DE 2418974 B1

The invention claimed is:

1. A process for preparing a compound of formula (I)

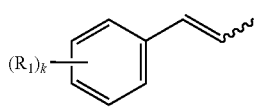

(I)

comprising contacting a compound of formula (II)

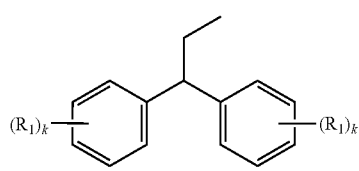

(II)

in the gas phase with a solid porous catalyst comprising silica, wherein
k is, independently from each other, 0, 1, 2 or 3;
R$_1$ is, independently from each other, hydroxy, C$_1$-C$_6$ alkoxy, di(C$_1$-C$_6$-alkyl) aminyl;
wherein the catalyst has a pore volume of at least 0.5 cm$^3$/g as determined by Hg porosimetry according to DIN 66133, and an acidity characterized by an amount of adsorbed ammonia of at most 0.1 mmol/g(catalyst) as determined by NH$_3$-TPD.

2. The process of claim 1, wherein the catalyst has a pore volume in the range of from 0.5 to 2.0 cm$^3$/g.

3. The process of claim 1, wherein the catalyst has a pore volume in the range of from 0.7 to 1.1 cm$^3$/g.

4. The process of claim 1, wherein the catalyst has an acidity characterized by an amount of adsorbed ammonia in the range of from 0.01 to 0.09 mmol/g(catalyst).

5. The process of claim 1, wherein the catalyst has an acidity characterized by an amount of adsorbed ammonia in the range of from 0.01 to 0.06 mmol/g(catalyst).

6. The process of claim 1, wherein at least 75 weight-% of the catalyst consist of silica.

7. The process of claim 1, wherein at least 99 weight-% of the catalyst consist of silica.

8. The process of claim 1, wherein at least 99.5 weight-% of the catalyst consist of silica and wherein the catalyst has a pore volume in the range of from 0.8 to 1.0 cm$^3$/g and an acidity characterized by an amount of adsorbed ammonia in the range of from 0.02 to 0.05 mmol/g(catalyst).

9. The process of claim 1, wherein the catalyst is in the form of moldings, having an essentially circular cross section, wherein the cross section has a diameter in the range of from 1 to 5 mm.

10. The process of claim 1 wherein C$_1$-C$_6$ alkoxy is selected from the group consisting of methoxy, ethoxy, n-propoxy, 1-methylethoxy, n-butoxy, 1-methylpropoxy, 2-methylpropoxy, 1,1-dimethylethoxy, n-pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy, and wherein in di($C_1$-$C_6$-alkyl) aminyl, the $C_1$-$C_6$-alkyl is selected from the group consisting of methyl, ethyl, propyl, isopropyl, n-butyl, isobutyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl and 1-ethyl-2-methylpropyl.

11. The process of claim 1, wherein the compound of formula (I) is a compound of formula

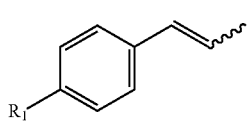
(I)

and the compound of formula (II) is a compound of formula

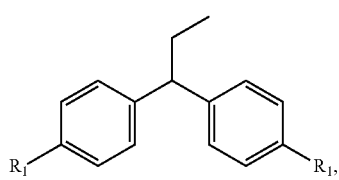
(II)

wherein the compound of formula (I) is a compound of formula

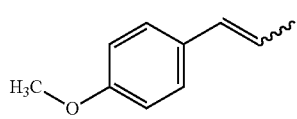
(I)

and the compound of formula (II) is a compound of formula

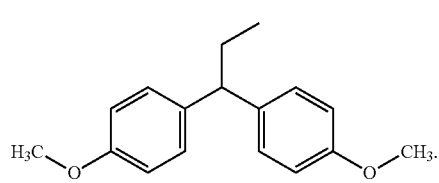
(II)

12. The process of claim 1, wherein contacting the compound of formula (II) with the solid porous catalyst comprising silica is carried out under thermolytic conditions at a temperature of the gas phase in the range of from 250 to 650° C., and at an absolute pressure of the gas phase in the range of from 0.1 to 2.0 bar.

13. The process of claim 1, wherein contacting the compound of formula (II) with the solid porous catalyst comprising silica is carried out under thermolytic conditions at a temperature of the gas phase in the range of from 300 to 400° C., and at an absolute pressure of the gas phase in the range of from 0.8 to 1.1 bar.

14. The process of claim 1, wherein contacting the compound of formula (II) with the solid porous catalyst comprising silica is carried out in the presence of water, and wherein the gas phase further comprises nitrogen.

15. The process of claim 1, wherein contacting the compound of formula (II) with the solid porous catalyst comprising silica is carried out in continuous mode.

16. The process claim 1, wherein contacting the compound of formula (II) with the solid porous catalyst comprising silica is carried out at a catalyst load in the range of from 0.01 to 5 kg(compound of formula (II))/kg(catalyst)/h.

17. The process of claim 1, wherein contacting the compound of formula (II) with the solid porous catalyst comprising silica is carried out at a catalyst load in the range of from 0.1 to 0.5 kg(compound of formula (II))/kg(catalyst)/h.

18. The process of claim 1, further comprising cooling the reaction mixture, obtained from contacting the compound of formula (II) in the gas phase with the solid catalyst, to a temperature in the range of from 0 to 40° C.

19. The process of claim 1, wherein the compound of formula (I) comprises a compound of formula (I-a)

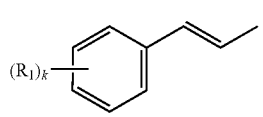
(I-a)

and a compound of formula (I-b)

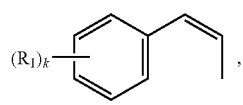
(I-b)

said process further comprising separating the compound of formula (I-a) from the compound of formula (I-b), by distillation.

20. A process for increasing the selectivity of solid catalyst gas-phase thermolysis of a compound of formula (II)

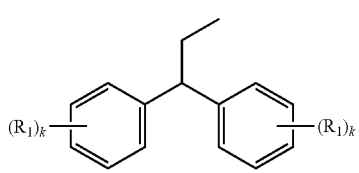
(II)

with respect to the compound of formula (I-a)

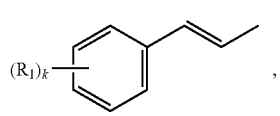
(I-a)

wherein
k is, independently from each other, 0, 1, 2 or 3;
$R_1$ is, independently from each other, hydroxy, $C_1$-$C_6$ alkoxy, di($C_1$-$C_6$-alkyl) aminyl, which comprises utilizing a solid porous catalyst comprising silica, wherein the catalyst has a pore volume of at least 0.5 cm³/g as determined by Hg porosimetry according to DIN 66133, and an acidity characterized by an amount of adsorbed ammonia of at most 0.1 mmol/g(catalyst) as determined by $NH_3$-TPD.

21. The process of claim 1, wherein the catalyst is in the form of strands having an essentially circular cross section, wherein the cross section has a diameter in the range of from 1 to 5 mm.

* * * * *